US011266856B2

(12) United States Patent
Jensen et al.

(10) Patent No.: US 11,266,856 B2
(45) Date of Patent: Mar. 8, 2022

(54) RADIOTHERAPY SYSTEM WITH LINEAR MOTOR FOR TRANSVERSE ACTUATION OF BASE AND ROTATION OF GANTRY

(71) Applicant: Varian Medical Systems, Inc., Palo Alto, CA (US)

(72) Inventors: David Jensen, Sunnyvale, CA (US); Stephen Gaudio, Mountain View, CA (US); Blake Gaderlund, Mountain View, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 359 days.

(21) Appl. No.: 15/957,745

(22) Filed: Apr. 19, 2018

(65) Prior Publication Data

US 2019/0099623 A1 Apr. 4, 2019

Related U.S. Application Data

(60) Provisional application No. 62/566,301, filed on Sep. 29, 2017.

(51) Int. Cl.
*A61N 5/10* (2006.01)
*H01H 13/02* (2006.01)
(Continued)

(52) U.S. Cl.
CPC ............ *A61N 5/1048* (2013.01); *A61B 6/461* (2013.01); *A61B 6/467* (2013.01); *H01H 9/161* (2013.01);
(Continued)

(58) Field of Classification Search
CPC ......... G01N 2223/30; G01N 2223/309; G01N 2223/32; G01N 2223/321; G01N 2223/3308; A61B 6/04; A61B 6/0407; A61B 6/0457; A61B 6/44; A61B 6/589; A61B 34/30; A61B 6/0414; A61B 6/0421; A61B 6/0428; A61B 6/0442; A61B 6/0464; A61B 6/0487; A61B 6/0492; A61B 6/4429; A61B 6/4435; A61N 5/10; A61N 5/1048; A61N 5/1049; A61N 5/1064; A61N 5/1069; A61N 5/107; A61N 2005/1057;
(Continued)

(56) References Cited

U.S. PATENT DOCUMENTS 5,448,607 A * 9/1995 McKenna ............... A61B 6/035
378/17
6,428,206 B1 * 8/2002 Watanabe ............ A61B 6/4233
378/197
(Continued)

*Primary Examiner* — Anastasia Midkiff
(74) *Attorney, Agent, or Firm* — SU IP Consulting

(57) ABSTRACT

A radiation therapy system includes a treatment couch positioning assembly that is directly coupled to a fixed structure supporting the linear accelerator of the radiation therapy system. The radiation therapy system can be installed in a radiation therapy facility without the floor of the facility being excavated and a sub-floor structure, such as a base frame, being installed. To laterally position a patient relative to the linear accelerator, the treatment couch positioning assembly of the radiation therapy system is laterally translated via a linear motor, and laterally translates with the treatment couch, rather than cantilevering the treatment couch to either side of the couch positioning assembly.

19 Claims, 7 Drawing Sheets

(51) Int. Cl.
  *H01H 9/16* (2006.01)
  *H01H 13/70* (2006.01)
  *A61B 6/00* (2006.01)
  *H05G 1/58* (2006.01)
  *H05G 1/56* (2006.01)
  *A61B 17/00* (2006.01)
  *H03K 17/18* (2006.01)
  *H03K 17/96* (2006.01)
  *H03K 17/955* (2006.01)
  *A61B 6/04* (2006.01)

(52) U.S. Cl.
  CPC .......... *H01H 13/023* (2013.01); *H01H 13/70* (2013.01); *H05G 1/56* (2013.01); *H05G 1/58* (2013.01); *A61B 2017/00017* (2013.01); *A61B 2017/00199* (2013.01); *A61N 2005/1074* (2013.01); *H01H 2013/026* (2013.01); *H01H 2239/064* (2013.01); *H01H 2300/014* (2013.01); *H01H 2300/038* (2013.01); *H01H 2300/04* (2013.01); *H03K 17/18* (2013.01); *H03K 17/96* (2013.01)

(58) Field of Classification Search
  CPC .... A61N 2005/1074; H01H 1/12; H01H 1/14; H01H 1/18; H01H 1/36; H01H 1/54; H01H 2001/545; H01H 2003/268; H03K 17/955; H01J 37/20; H01J 2237/02; H01J 2237/20; H01J 2237/20207; H01J 2237/20221; H01J 2237/20228; H01J 2237/20278; H01J 2237/20292
  See application file for complete search history.

(56) References Cited

U.S. PATENT DOCUMENTS

| | | | |
|---|---|---|---|
| 9,109,743 B2 * | 8/2015 | Schwab | B23Q 1/5462 |
| 2002/0180397 A1 * | 12/2002 | Henley | A61B 6/0457 |
| | | | 318/687 |
| 2007/0197908 A1 * | 8/2007 | Ruchala | A61B 6/0487 |
| | | | 600/427 |
| 2010/0102239 A1 * | 4/2010 | Hahn | G06T 5/50 |
| | | | 250/363.05 |
| 2012/0076269 A1 * | 3/2012 | Roberts | A61N 5/1049 |
| | | | 378/65 |
| 2014/0046212 A1 * | 2/2014 | Deutschmann | A61B 6/4452 |
| | | | 600/567 |
| 2014/0341351 A1 * | 11/2014 | Berwick | A61N 5/1045 |
| | | | 378/65 |
| 2015/0078514 A1 * | 3/2015 | Pettinato | A61B 6/0407 |
| | | | 378/20 |
| 2016/0302871 A1 * | 10/2016 | Gregerson | A61B 34/30 |
| 2017/0325754 A1 * | 11/2017 | Pettinato | A61B 6/0407 |
| 2018/0016881 A1 * | 1/2018 | Etter | H02K 41/02 |

* cited by examiner

RADIOTHERAPY SYSTEM WITH LINEAR MOTOR FOR TRANSVERSE ACTUATION OF BASE AND ROTATION OF GANTRY

CROSS-REFERENCE TO RELATED APPLICATION

The present application claims the benefit of U.S. Provisional Application No. 62/566,301, filed Sep. 29, 2017. The aforementioned U.S. Provisional Application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

Radiation therapy, which is the use of ionizing radiation, is a localized treatment for a specific target tissue, such as a cancerous tumor. Ideally, radiation therapy is performed on target tissue (also referred to as the planning target volume) that spares the surrounding normal tissue from receiving doses above specified tolerances, thereby minimizing risk of damage to healthy tissue. So that the prescribed dose is correctly supplied to the planning target volume during radiation therapy, the patient should be precisely positioned relative to the linear accelerator that provides the radiation therapy, typically with a movable treatment couch mounted on a turntable assembly. One challenge of radiation therapy is to ensure that the movable treatment couch is precisely located relative to the linear accelerator and other components of the radiation therapy system during installation, since an inaccurately located treatment couch can adversely affect accuracy of radiation dosing delivered by the system.

In a conventional radiation therapy system, a base frame is typically employed to ensure that the turntable assembly for the treatment couch is accurately positioned relative to the linear accelerator of the radiation therapy system. A base frame is a below-floor structure that is installed in a pit excavated from the floor of a radiotherapy facility, and provides structural attachments for the treatment couch turntable assembly and for the support structure of the linear accelerator. In addition, the base frame provides precise alignment and relative positioning of the components coupled thereto, including the treatment couch assembly and the support structure of the linear accelerator. Thus, once the base frame has been embedded in the floor and the turntable assembly and linear accelerator support have been coupled to the base frame, the location of the treatment couch relative to the linear accelerator is known to a high degree of precision. However, installations of such radiation therapy systems require extensive and time-consuming site preparation. Further, the base frame itself adds significant weight and material cost to the radiation therapy system.

In light of the above, there is a need in the art for radiation therapy systems that address the above-described challenges.

BRIEF DESCRIPTION OF THE DRAWINGS

Features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
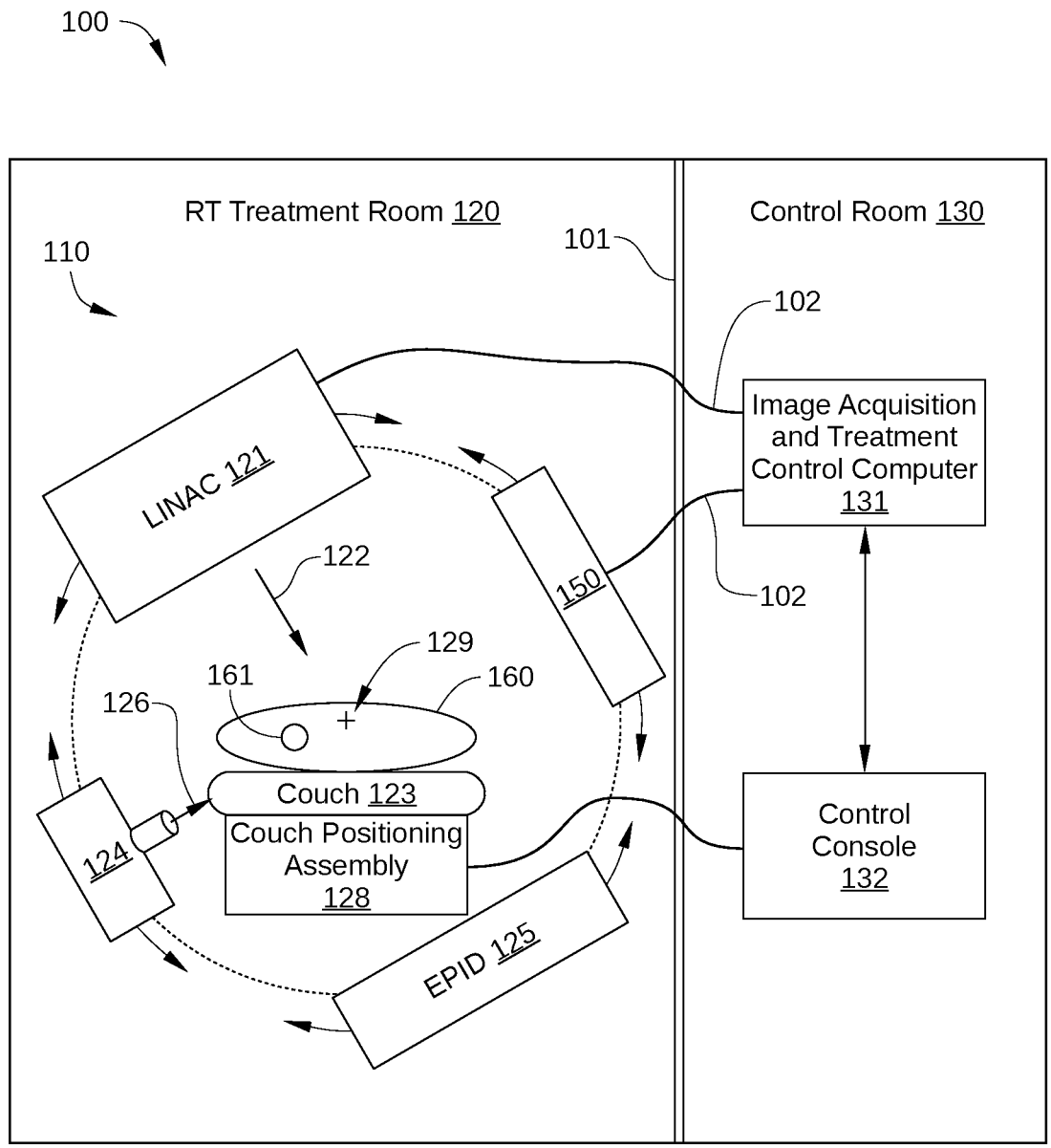
FIG. 1 illustrates a clinical environment in which an embodiment of the present disclosure can be integrated.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As noted above, when radiation treatment is applied accurately to targeted tissue in a patient via a radiation therapy (RT) system, there is minimal impact on healthy tissue surrounding the targeted tissue. Further, precisely positioning the treatment couch and the structure supporting the linear accelerator of the RT system is a significant factor in accurately targeting tissue in the patient. According to various embodiments, an RT system includes a treatment couch positioning assembly that is directly coupled to a structure supporting the linear accelerator of the RT system. Consequently, the RT system can be installed in an RT facility without the floor of the facility being excavated and a sub-floor structure, such as a base frame, being installed. In addition, the treatment couch positioning assembly of the RT system is configured to laterally position a patient relative to the linear accelerator by laterally translating with the treatment couch, rather than cantilevering the treatment couch to either side of the couch positioning assembly.

FIG. 1 illustrates a clinical environment 100 in which an embodiment of the present disclosure can be integrated. Clinical environment 100 includes a RT treatment room 120 with an RT treatment system 110 disposed therein and a control room 130, separated by a shielded wall 101. RT treatment system 110 includes a linear accelerator (LINAC) 121 that generates a megavolt (MV) treatment beam 122 of high energy X-rays (or in some embodiments electrons), a patient table or treatment couch 123 mounted on a couch positioning assembly 128, a kilovolt (kV) X-ray source 124, an X-ray imager 150, and, in some embodiments, an MV electronic portal imaging device (EPID) 125. Control room 130 includes an image acquisition and treatment control computer 131 communicatively coupled to X-ray imager 150 and LINAC 121 wirelessly or via acquisition cables 102, and a control console 132 for controlling couch positioning assembly 128.

Also shown in FIG. 1 is a patient 160, positioned on treatment couch 123 for RT treatment. Patient 160 includes a target region 161. Target region 161 may be, for example, a tumor to receive RT treatment, and can be located in different regions of the body of patient 160, such as the head, thorax, or leg. Typically, couch positioning assembly 128 is configured to position patient 160 so that target region 161 is at or near an isocenter 129 about which LINAC 121, EPID 125, kV X-ray source 124, and X-ray imager 150 are rotated during RT treatment.

LINAC 121 customizes treatment beam 122 to conform to the shape of a tumor in target region 161 of patient 160. Thus, LINAC 121 destroys cancer cells while sparing surrounding normal tissue when the location of target region 161 is precisely known. kV X-ray source 124 is an X-ray source for generating an imaging beam 126, which is directed toward X-ray imager 150 for imaging target region 161 and surrounding areas during RT treatment. For example, in some embodiments, clinical environment 100 is employed for image-guided radiation therapy (IGRT), which uses image guidance procedures for target localization before and during treatment. In such embodiments, the images used to precisely monitor the current location of target region 161 are generated with kV X-ray source 124 and X-ray imager 150. Alternatively or additionally, in some embodiments, images generated with kV X-ray source 124 and X-ray imager 150 can be employed in intensity-modulated radiation therapy (IMRT) applications. In either IGRT or IMRT applications, elements of RT treatment system 110 rotate about treatment couch 123 during RT treatment. For example, in some embodiments, LINAC 121, EPID 125, kV X-ray source 124, and X-ray imager 150 rotate about treatment couch 123 as shown. One embodiment of RT treatment system 110 is described below in conjunction with FIG. 2.

Figure 2:
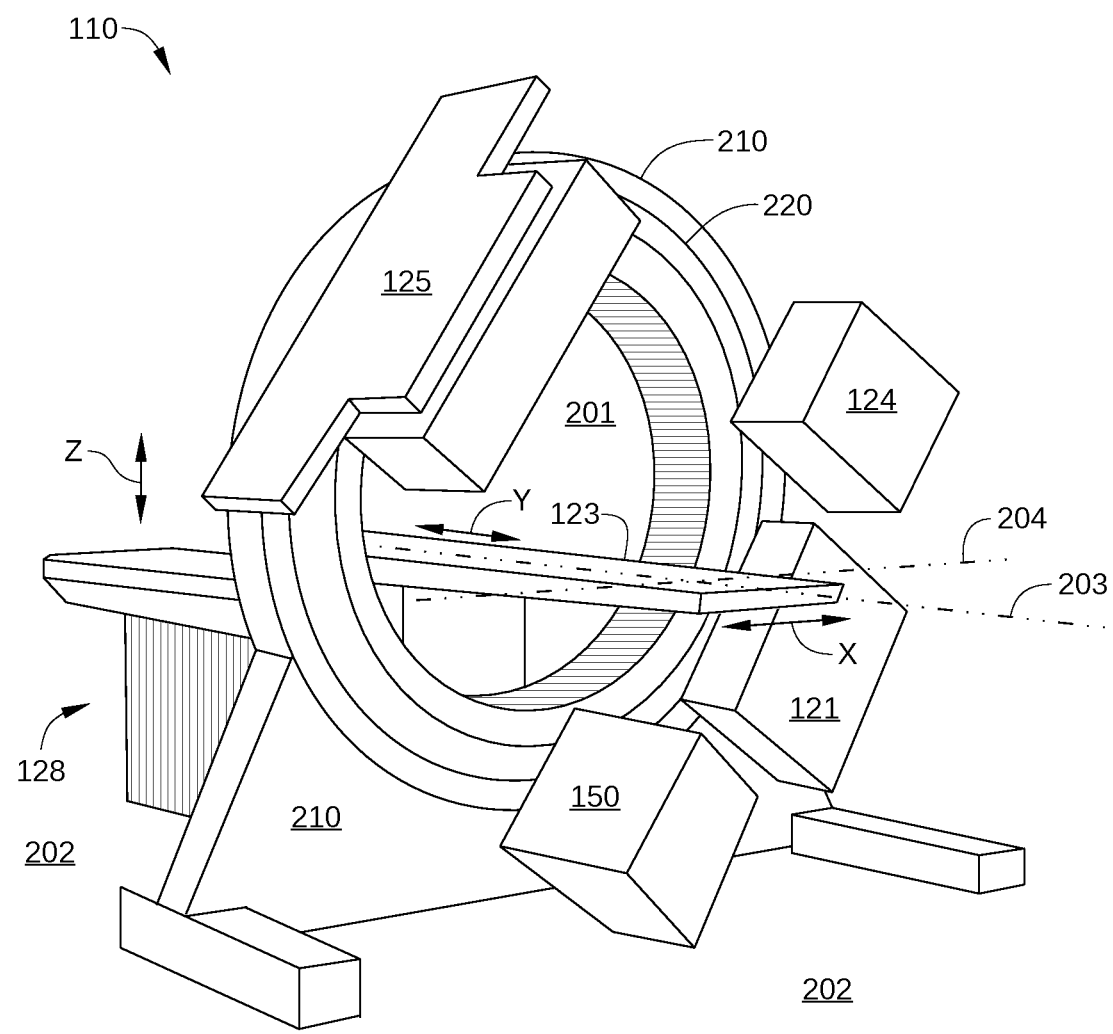
FIG. 2 schematically illustrates a perspective view of an RT treatment system, according to various embodiments of the present disclosure.

FIG. 2 schematically illustrates a perspective view of RT treatment system 110, according to various embodiments of the present disclosure. In FIG. 2, elements of RT treatment system 110 (LINAC 121, EPID 125, kV X-ray source 124, and X-ray imager 150) are shown partially rotated about treatment couch 123 at a specific point in time during operation, and treatment couch 123 is shown longitudinally extended from couch positioning assembly 128 into a bore 201 of RT treatment system 110. In the embodiment illustrated in FIG. 2, RT treatment system 110 further includes a drive stand 210 that is mechanically coupled to couch positioning assembly 128 and structurally supports a gantry 220.

Drive stand 210 is a fixed support structure for components of RT treatment system 110, including gantry 220, a drive system (not shown) for rotatably moving gantry 220, cooling systems (not shown) of RT treatment system 110, and the like. Drive stand 210 rests on and/or is fixed to a support surface 202 that is external to RT treatment system 110, such as a floor of an RT treatment facility. Gantry 220 is a rotatable support structure on which LINAC 121, EPID 125, kV X-ray source 124, and X-ray imager 150 are mounted. During operation of RT treatment system 110, gantry 220 rotates about bore 201.

Couch positioning assembly 128 is mechanically coupled to drive stand 210 and is configured to adjustably position treatment couch 123 relative to bore 201 and LINAC 121. In the embodiment illustrated in FIG. 2, couch positioning assembly 128 is configured to position treatment couch 123 along lateral directions X, longitudinal directions Y, and vertical directions Z. Movement of treatment couch 123 along lateral directions X corresponds to horizontal movement toward one side or the other side of bore 201, along longitudinal directions Y corresponds to horizontal movement into or out of bore 201, and along vertical directions Z corresponds to vertical movement toward or away from support surface 202. It is noted that couch positioning assembly 128 is rotatably fixed. As a result, when couch positioning assembly 128 positions treatment couch 123 along lateral directions X, longitudinal directions Y, and/or vertical directions Z, a longitudinal axis 203 of treatment couch 123 remains oriented in a single direction, i.e., towards bore 201, and a lateral axis 204 of treatment couch 123 remains oriented in a direction perpendicular to longitudinal axis 203 and toward the sides of bore 201. Thus, in the embodiment illustrated in FIG. 2, couch positioning assembly 128 translates treatment couch 123 relative to drive stand 210 and LINAC 121, but does not rotate treatment couch 123 about a lateral axis, a longitudinal axis, or a vertical axis. Couch positioning assembly 128 is described in greater detail below in conjunction with FIG. 3.

Figure 3:
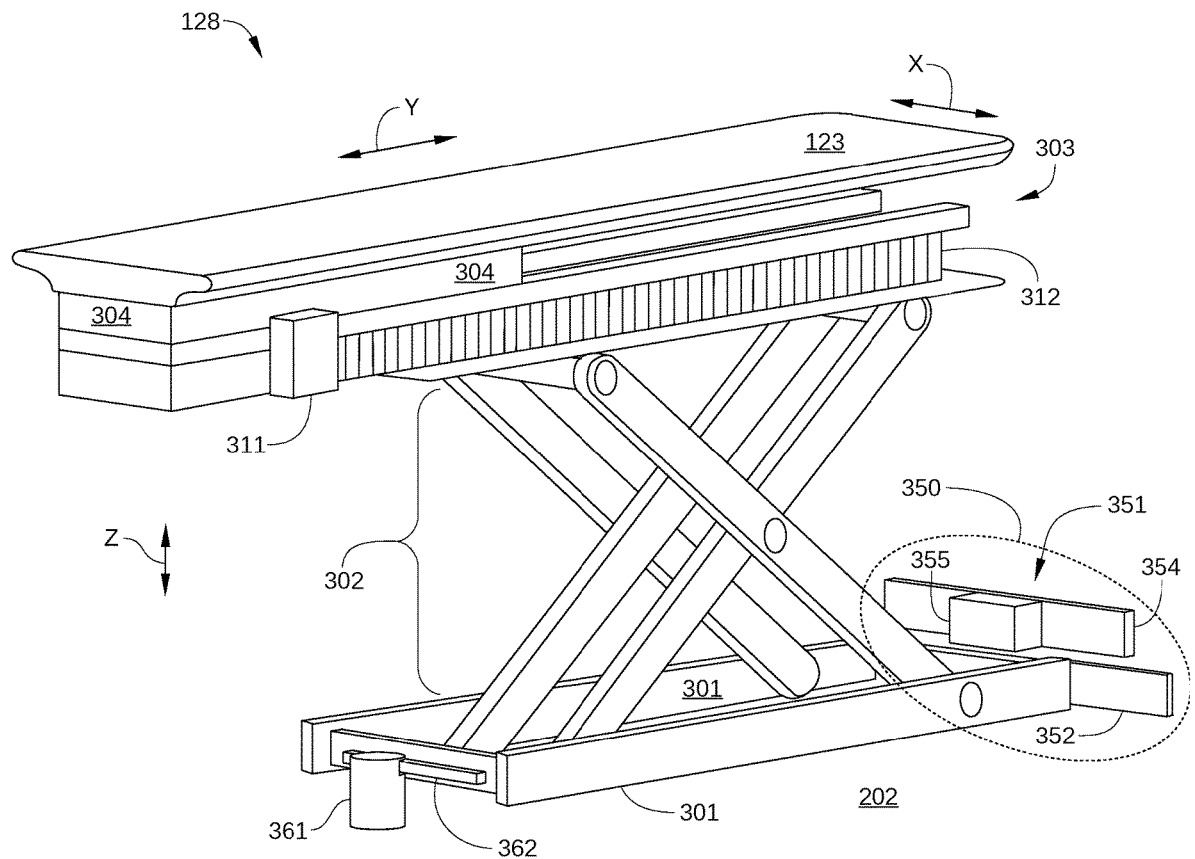
FIG. 3 schematically illustrates a perspective view of a couch positioning assembly, according to an embodiment of the present disclosure.

FIG. 3 schematically illustrates a perspective view of couch positioning assembly 128, according to an embodiment of the present disclosure. In FIG. 3, couch positioning assembly 128 is depicted with external panels removed for clarity. In the embodiment illustrated in FIG. 3, couch positioning assembly 128 includes a lift base 301 with a scissor lift mechanism 302 and a longitudinal frame 303 mounted thereon. Coupled to longitudinal frame 303 is a longitudinal carriage 304 that is translated along longitudinal axis Y via a longitudinal motor 311. Treatment couch 123 is mounted on and longitudinally moved by longitudinal carriage 304.

Scissor lift mechanism 302 is configured to translate treatment couch 123 in vertical directions Z, and can include any technically feasible actuation system. For example, in some embodiments, scissor lift mechanism 302 includes an electric motor, a hydraulic actuator, a stepper motor, or any other suitable actuation system for moving treatment couch 123 via scissor lift mechanism 302.

Longitudinal motor 311 is configured as a portion of a linear motor, which is an electric motor with the stator and rotor "unrolled," so that a linear force along the length of the motor is produced instead of torque. In the embodiment illustrate in FIG. 3, longitudinal motor 311 includes the linearly translating portion of the linear motor, such as the motor windings, bearings, position capture sensors, and the like. A longitudinal magnet track 312 makes up the portion of the linear motor that remains stationary, and is mounted on longitudinal frame 303. In conjunction with longitudinal magnet track 312, longitudinal motor 311 precisely and repeatably translates longitudinal carriage 304 and treatment couch 123 in longitudinal directions Y.

Couch positioning assembly 128 is also configured to precisely position treatment couch 123 in lateral directions X. More specifically, couch positioning assembly 128 is configured so that lift base 301 can be translated in lateral directions X relative to support surface 202. Thus, when lift base 301 is translated in lateral directions X, the components of couch positioning assembly 128 that are mounted on lift base 301, including treatment couch 123, are also translated in lateral directions X. By contrast, in conventional RT systems, an upper stage of a couch positioning assembly that includes the treatment couch is translated laterally while the remainder of the couch positioning assembly remains fixed laterally. However, lateral motion of such an upper stage causes the patient load to be moved off the center of the couch positioning assembly, resulting in torsional twisting deflection loads that decrease the positioning accuracy of the treatment couch. Instead, according to embodiments of the present disclosure, lift base 301 and the components mounted thereon (for example, scissor lift mechanism 302, longitudinal frame 303, longitudinal carriage 304, and treatment couch 123) are all laterally shifted together, keeping treatment couch 123 centered over lift base 301. Thus, the modes of deflection associated with treatment couch 123 being moved off the center of lift base 301 are minimized or eliminated, thereby increasing the positioning accuracy of RT system 100.

To implement lateral translation of lift base 301 as described above, in some embodiments, couch positioning assembly 128 is configured to be translated in lateral directions X relative to support surface 202 via a lateral carriage assembly 350. Lateral carriage assembly 350 includes a linear motor 351 that selectively urges lift base 301 in either of lateral directions X along a lateral rail 352 that is mounted to drive stand 210 (not shown). Linear motor 351 provides precise and repeatable motion of treatment couch 123 with respect to drive stand 210. Linear motor 351 includes a stator 354, which includes a magnet track, and a slider 355, which includes the rotor or windings of linear motor 351 that move along the magnet track. In the embodiment illustrated in FIG. 3, stator 354 is fixed to drive stand 210 and slider 355 is mounted to lift base 301. Thus, actuation of linear motor 351 causes slider 355 to urge lift base along lateral rail 352, thereby translating lift base 301 in one of lateral directions X relative to drive stand 210. Alternatively, stator 354 is fixed to lift base 301 and slider 355 is mounted to drive stand 210.

To further facilitate lateral motion of lift base 301 via lateral carriage assembly 350, an end of lift base 301 that is opposite to the end coupled to lateral carriage assembly 350 is configured to move laterally along a second lateral rail 362. In some embodiments, second lateral rail 362 is coupled to a single support, such as a pivot 361, which is fixed to support surface 202. Pivot 361 prevents over-constraint of the end of lift base 301 associated with second lateral rail 362. During lateral translation of lift base 301, lift base 301 rides on lateral rail 352 and second lateral rail 362, for example, via bearings (not shown) included in lateral carriage assembly 350 and pivot 361 that movably contact lateral rail 352 and second lateral rail 362. One embodiment of lateral carriage assembly 350 is illustrated in FIGS. 4 and 5.

Figure 4:
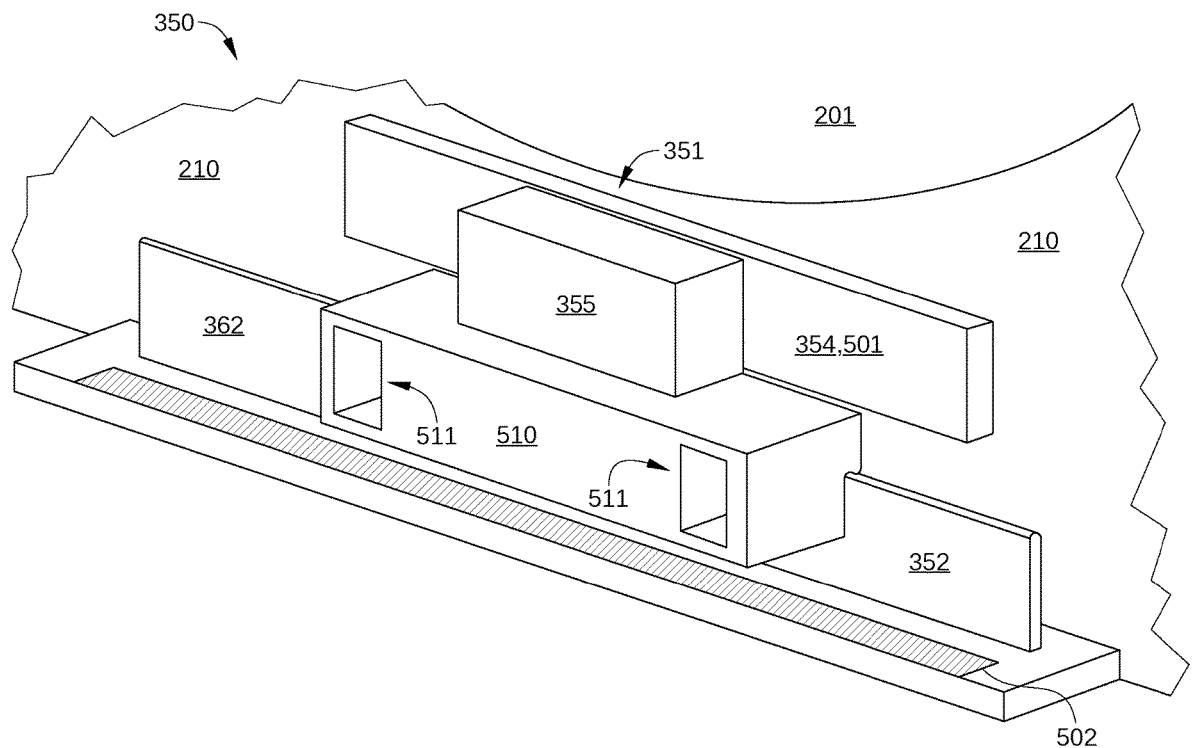
FIG. 4 schematically illustrates a perspective view of a lateral carriage assembly, according to an embodiment of the present disclosure FIG. 5 schematically illustrates a side view of a lateral carriage assembly, according to an embodiment of the present disclosure.
Figure 5:
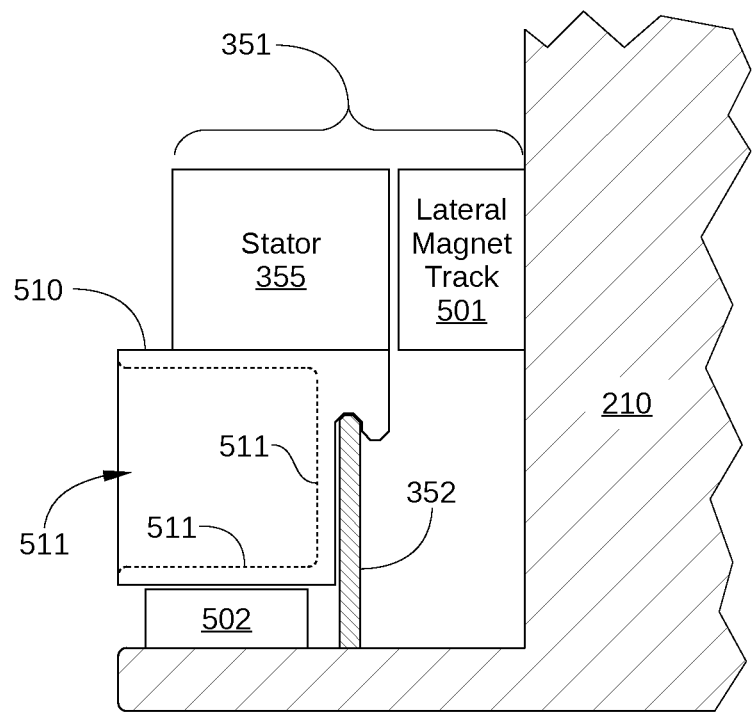

FIG. 4 schematically illustrates a perspective view and FIG. 5 schematically illustrates a side view of lateral carriage assembly 350, according to an embodiment of the present disclosure. As shown, lateral carriage assembly 350 includes linear motor 351, an encoder strip 502 that provides position feedback for lateral carriage assembly 350, and a coupling mechanism 510 that includes one or more interface features 511. In the embodiment illustrated in FIGS. 4 and 5, linear motor 351 includes stator 354, which has a lateral magnet track 501, and slider 355. Coupling mechanism 510 and interface features 511 enable precise alignment and positioning between lift base 301 and drive stand 210. For example, when interface features 511 include precision machined mounting features that contact corresponding interface features that are disposed on lift base 301 (not shown in FIG. 4 or 5), the position of lift base 301 relative to drive stand 210. Therefore the position of treatment couch 123 relative to LINAC 125 can be known with high precision.

In some embodiments, interface features 511 include one or more machined surfaces, alignment pins, alignment holes, and the like. Similarly, the interface features disposed on lift base 301 that correspond to interface features 511 can include, as appropriate, one or more machined surfaces, alignment pins, alignment holes, and the like. In the embodiment illustrated in FIGS. 4 and 5, each of interface features 511 is configured as an alignment hole with one or more machined surfaces configured to contact a corresponding surface of a protuberance or other interface feature precisely positioned on lift base 301. An embodiment of such interface features on lift base 301 is illustrated in FIG. 6.

Figure 6:
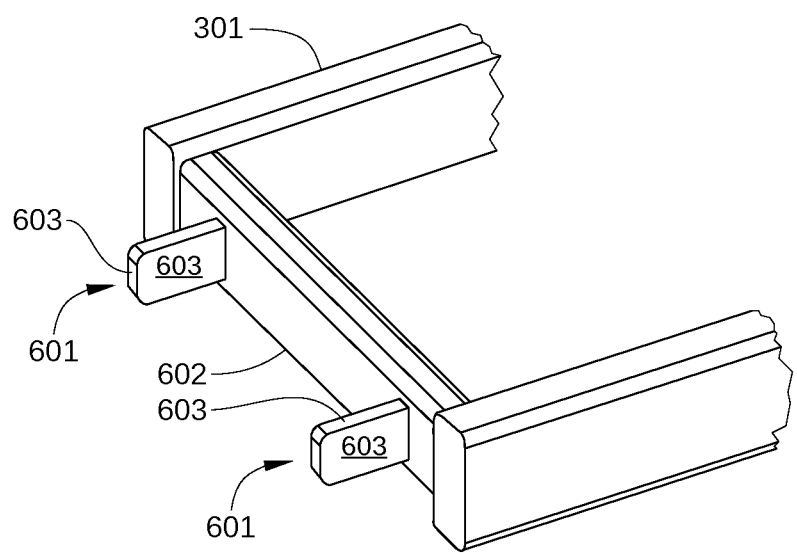
FIG. 6 schematically illustrates a perspective view of interface features disposed on a lift base, according to an embodiment of the present disclosure.

FIG. 6 schematically illustrates a perspective view of interface features 601 disposed on lift base 301, according to an embodiment of the present disclosure. As shown, lift base 301 includes interface features 601, which are precisely positioned on an end 602 of lift base 301 proximate drive stand 210 (not shown). In some embodiments, interface features 601 each include one or more machined or otherwise precisely located surfaces 603 that each contact a corresponding surface of an interface feature 511 included in lateral carriage assembly 350.

Figure 7:
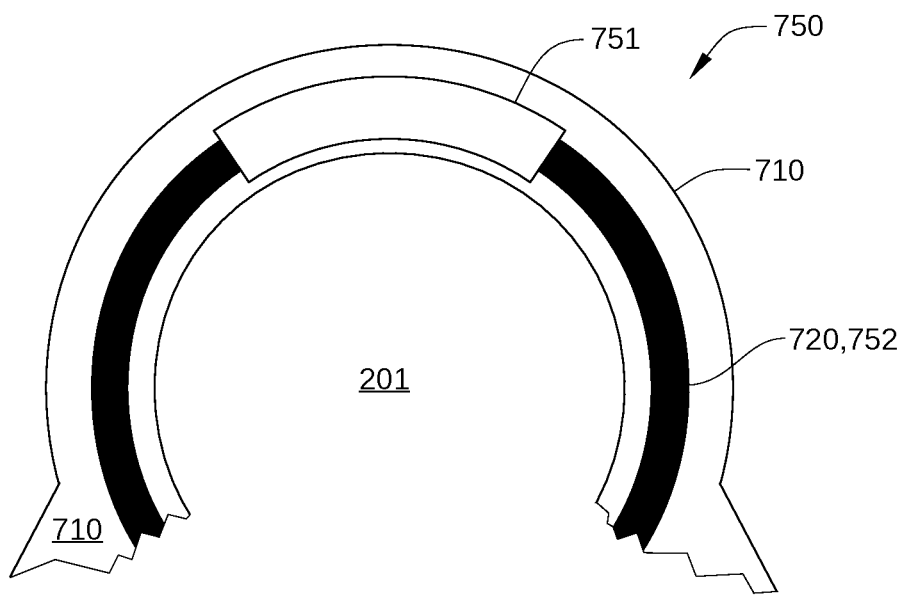
FIG. 7 schematically illustrates a drive stand with a gantry that is rotationally actuated by a linear motor, according to an embodiment of the present disclosure.

In some embodiments, RT treatment system 100 also includes rotational actuation of a gantry via a linear motor that has a curved configuration. One such embodiment is illustrated in FIG. 7. FIG. 7 schematically illustrates a drive stand 710 with a gantry 720 that is rotationally actuated by a linear motor 750, according to an embodiment of the present disclosure. Gantry 720 is substantially similar in configuration to gantry 220 in FIG. 2, except that gantry 720 is actuated via linear motor 750. In the embodiment illustrated in FIG. 7, a gantry rotation motor 751 is fixed, for example by being coupled to a portion of drive stand 710, while a gantry rotation magnet track 752 is coupled to or mounted on gantry 720, which rotates when in operation. Components that are mounted on or fixed to gantry 720 are not shown for clarity, but may include the beam generating components, beam limiting components such as collimation and beam stop, and image acquisition elements, such as EPID 125 and/or X-ray imager 150 (shown in FIG. 1). These movable components are rotated about bore 201 in by gantry 720.

It is noted that the linear motor actuators employed for rotation of gantry 720, longitudinal actuation of treatment couch 123, and lateral actuation of lift base 310 are highly beneficial compared to prior art techniques. Specifically, the herein-described linear motors have improved accuracy, since the motor is coupled directly to the load. In addition, over conventional apparatus and techniques known in the art, the herein-described linear motors have improved acceleration, speed, simplicity, (due to having fewer parts than conventional actuators) and improved reliability (due to having fewer parts undergoing wear than conventional actuators).

It is further noted that directly coupling lift base 301 to drive stand 210 via precisely located features, such as interface features 511 and 601, rigidly fixes the orientation and position of couch positioning assembly 128 and LINAC 121 relative to each other. Because the precision interface between lift base 301 and drive stand 210, such as that included in lateral carriage assembly 350, is what provides the precise connection between treatment couch 123 and gantry 220, no base frame is needed. Thus, the footprint of RT treatment system is greatly reduced and less site preparation is needed compared to conventional RT systems. Instead of excavating a floor for installation of a base frame, drive stand 210 is bolted or otherwise fixed to support surface 202, couch positioning assembly 128 is coupled to drive stand 210 (via lateral carriage assembly 350), and couch positioning assembly 128 is movably coupled to support surface 202 via pivot 361.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A radiation treatment system comprising:
a fixed support structure that is fixed to a support surface external to the radiation treatment system;
a radiation source that emits a treatment beam toward a bore of the radiation treatment system, is rotatably coupled to the fixed support structure, and rotates about the bore;
a movable treatment couch that is coupled to a couch positioning assembly and is configured to position a patient relative to the fixed support structure, wherein the movable treatment couch includes a longitudinal axis oriented toward the bore and a lateral axis that is perpendicular to the longitudinal axis; and
the couch positioning assembly, wherein the couch positioning assembly is movably coupled to the fixed support structure and is translatable relative to the fixed support structure via a linear motor in a direction parallel to the lateral axis.

2. The radiation treatment system of claim 1, wherein the couch positioning assembly includes a first end that is coupled to a lateral carriage assembly that includes the linear motor.

3. The radiation treatment system of claim 2, wherein the lateral carriage assembly translates in the direction parallel to the lateral axis along a rail mounted on the fixed support structure.

4. The radiation treatment system of claim 3, further comprising an encoder strip mounted on the fixed support structure and disposed proximate the rail.

5. The radiation treatment system of claim 2, wherein the first end is positioned relative to the fixed support structure via at least one interface feature included in the lateral carriage assembly.

6. The radiation treatment system of claim 5, wherein the first end includes a locating feature configured to contact the at least one interface feature included in the lateral carriage assembly.

7. The radiation treatment system of claim 2, wherein the couch positioning assembly includes a second end that translates in the direction parallel to the lateral axis along a rail coupled to the support surface external to the radiation treatment system.

8. The radiation treatment system of claim 7, wherein the rail is coupled to the support surface via a single pivot mechanism.

9. The radiation treatment system of claim 7, wherein the fixed support structure rests on the support surface.

10. The radiation treatment system of claim 1, wherein the radiation source is rotatably coupled to the fixed support structure via a linear motor with a curved configuration that rotates a rotatable support structure about the movable treatment couch.

11. The radiation treatment system of claim 1, wherein the couch positioning assembly is rotatably fixed so that the longitudinal axis remains oriented in a single direction.

12. The radiation treatment system of claim 1, wherein the couch positioning assembly is fixed relative to the fixed support structure in a direction parallel with the longitudinal axis.

13. The radiation treatment system of claim 12, wherein the couch positioning assembly includes a linear motor configured to position the movable treatment couch relative to the fixed support structure in a direction parallel with the longitudinal axis.

14. The radiation treatment system of claim 1, wherein the couch positioning assembly is configured to position the movable treatment couch relative to the fixed support structure in a vertical direction.

15. A couch positioning assembly in a radiation treatment system, the couch positioning assembly comprising:
a movable treatment couch that is configured to position a patient relative to a fixed support structure of the radiation treatment system in a direction parallel with a longitudinal axis of the movable treatment couch, wherein the fixed support structure is fixed to a support surface external to the radiation treatment system and is rotatably coupled to a radiation source that emits a treatment beam;
a mechanism that is configured to position the movable treatment couch in a direction perpendicular to the longitudinal axis and to a lateral direction that is perpendicular to the longitudinal axis; and
a lateral carriage assembly that is movably coupled to the fixed support structure and includes a linear motor configured to simultaneously translate the mechanism and the movable treatment couch in the lateral direction, wherein the longitudinal axis of the movable treatment couch is oriented toward the fixed support structure.

16. The couch positioning assembly of claim 15, wherein the lateral carriage assembly further includes a first lateral rail that is fixed to the fixed support structure and along which the lift base is translated by the linear motor.

17. The couch positioning assembly of claim 16, wherein the lift base includes a second lateral rail that is parallel to the first lateral rail and is coupled to the support surface.

18. The couch positioning assembly of claim 17, wherein the second lateral rail is coupled to the support surface via a single pivot that is fixed to the support surface.

19. The couch positioning assembly of claim 15, wherein the lateral direction is parallel to the support surface.

* * * * *